United States Patent [19]

Groman

[11] 4,250,162

[45] Feb. 10, 1981

[54] PROTEIN BINDING METHOD

[75] Inventor: Ernest V. Groman, Brookline, Mass.

[73] Assignee: Baxter Travenol Laboratories, Inc., Deerfield, Ill.

[21] Appl. No.: 54,080

[22] Filed: Jul. 2, 1979

[51] Int. Cl.³ .................. G01N 33/56; G01N 33/78
[52] U.S. Cl. .................................. 424/1; 23/230 B; 23/915; 23/920; 23/923
[58] Field of Search ............... 424/1, 12; 23/230 B, 23/915, 920, 923

[56] References Cited

U.S. PATENT DOCUMENTS

| | | | |
|---|---|---|---|
| 3,646,346 | 2/1972 | Catt | 23/230 B X |
| 3,929,981 | 12/1975 | Murty et al. | 230/230 B X |
| 4,081,525 | 3/1978 | Knight et al. | 23/230 B X |

OTHER PUBLICATIONS

Makin, "Biochemistry of Steriod Hormones," Blackwell Scientific Publications, Oxford, 1975, pp. 185-192.

*Primary Examiner*—Arnold Turk
*Attorney, Agent, or Firm*—Paul C. Flattery; Lawrence W. Flynn; Max D. Hensley

[57] ABSTRACT

Samples are extracted with organic solvents and the organic solvents are then placed directly into antiserum coated test tubes and dried. The improved method combines steps heretofore performed separately, resulting in improved assay convenience, cost and accuracy.

15 Claims, No Drawings

PROTEIN BINDING METHOD

BACKGROUND OF THE INVENTION

This invention relates to analytical methods wherein samples are extracted with organic solvents to obtain analytes free of unextracted sample constituents such as proteins, followed by specific protein binding assays for the extracted analytes. In particular, this invention relates to those methods in which substantially water immiscible organic solvents have been used in such extractions.

Specific protein binding assays are defined herein as methods for analysis which exploit the capacity of various proteins to reversibly bind other substances with varying degrees of specificity. Such assays are in general well known. Exemplary specific protein binding assays are the sandwich, sequential saturation, and competitive methods. Such assays usually employ an antiserum which contains antibodies capable of reversibly, specifically binding the substance to be determined, i.e., the analyte. However, naturally occurring, non-immune binding proteins such as intrinsic factor and thyroxine binding globulin have been used satisfactorily as specific binding proteins. The analytes which can be determined by specific protein binding assays are virtually limitless; if a non-immune protein specific for the analyte cannot be found then an antibody having the desired specificity can be raised by known techniques.

The method of this invention particularly relates to those analytes such as hormones and drugs, generally low molecular weight substances, which are soluble to at least some extent in organic solvents.

It has been conventional practice in specific protein binding assays for such analytes to extract the analyte-containing samples with organic solvents. This has been done primarily for three reasons. First, organic solvents are well-known protein denaturing agents. Since many analytes are noncovalently bound by endogenous body fluid proteins it has been considered desirable to release the analyte from the proteins so that it can be determined along with the proportion of analyte which is normally free. Organic solvents may achieve the desired release of analyte by denaturing the binding proteins.

Second, water immiscible solvent extraction has been useful to extract analytes from mixtures containing related compounds. For example, cortisol and estriol may be solvent extracted from their sulfate and glucuronide derivatives.

Third, water immiscible organic solvents have been employed to extract analytes found in samples at low concentrations. The solvent in the extracts is then removed and the residue taken up in a small amount of aqueous solution, thereby concentrating the analyte to a degree dependent upon the volume of reconstituting solution. Also, such solvents frequently have the effect noted above of freeing the analyte from endogenous binding proteins. The term "extraction" of a sample as used herein means extraction of sample analyte from the aqueous phase, with or without extraction of analyte bound to endogenous binding proteins or exclusion of substances related to the analyte of interest.

The organic solvents which have been employed for the above purposes are substantially water immiscible organic solvents, i.e. carbon-containing compounds which are liquid at one atmosphere pressure, partially or wholly within the range of greater than about 0° C. and less than about 100° C. Substantially water immiscible organic solvents are defined as organic solvents which are soluble in water at 20° C. to the extent of less than about 15% v/v. Exemplary organic solvents that have been used heretofore for extraction include carbon tetrachloride, methylene chloride (dichloromethane), ethyl ether, ethyl acetate, petroleum ether, diethyl ether, ether, and benzene. Ordinarily the organic solvents are simply mixed with the sample, e.g., homogenized tissue, blood serum or urine, and incubated for a period sufficient to extract the desired substance. The organic layer is removed and evaporated, and the dry analyte then assayed.

Specific protein binding assays are frequently performed using insoluble surfaces physically coated with the binding proteins as opposed to the more difficult to manufacture covalently bound proteins. Such surface absorbed proteins are used in the assays to separate the protein bound analyte from that which remains in the liquid phase. One particularly popular technique is to absorb specific antibody onto the inner surface of a plastic test tube, usually polypropylene. See for example U.S. Pat. No. 3,646,346. Such test tubes are used in a typical competitive immunoassay by first adding aqueous solutions of the analyte and a labeled analogue of the analyte, or tracer, to a tube. After an incubation period to allow the tracer and analyte to compete for a limited number of protein binding sites, the protein-bound population of tracer and analyte is then separated from the population which remains in solution. This is conveniently done by decanting or aspirating the reaction solution from the tube.

The prior art has almost uniformly viewed the solvent extraction of samples to be a procedure separate and distinct from the specific binding assay. The practice of the prior art has been to completely remove the organic solvent employed in the sample extraction before the residual analyte is contacted with any of the reagents employed in the specific binding assay, e.g., antibody. Ordinarily the complete process has entailed removing the extract to a container, evaporating the solvent, resolubilizing the dry residue and then adding the reagents needed for the specific protein assay. This is clearly inconvenient, labor intensive and susceptible to considerable experimental error. However, the prior art has in at least one instance included organic solvent in the reagents used to perform a specific binding assay. According to U.S. Pat. No. 4,081,525, from about 0% to about 10% of a water miscible organic solvent can be used to extract steroids from carrier proteins present in samples while simultaneously conducting a specific protein binding assay. This method is of limited utility because, first, it provides for such a low concentration of organic solvent that the extraction efficiency may be unsatisfactory and, second, the solvent must be water miscible and therefore cannot be used to concentrate the sample analyte.

OBJECTS OF THE INVENTION

It is accordingly an object of this invention to render more convenient, less costly and more accurate, those specific protein binding assays which in the prior art have been preceded by a separate organic solvent extraction of the sample to be determined.

It is an additional object of this invention to render more convenient, less costly and more accurate those assays wherein substantially water-immiscible organic solvents have been used for the sample extraction.

These and other objects of the invention will be apparent from consideration of the invention as a whole.

SUMMARY OF THE INVENTION

The above objects are achieved, in a method for determining the concentration of an analyte in a sample wherein the sample is extracted with a substantially water immiscible organic solvent, the solvent removed from the extract and the extract assayed by a specific protein binding assay, by the improvement comprising removing the solvent from the extract while the solvent is in contact with a surface-absorbed binding protein specific for said analyte.

The direct contact of the organic solvent with surface-absorbed protein which is contemplated by this method does not adversely affect the performance of the protein in the binding assay and, where the protein is absorbed onto a surface of an organic polymer, any deposition of analyte onto or into the polymer by the solvent is insufficient to adversely affect the assay results, on the order of less than 5% absorption of analyte, usually less than 3%, which analyte is freely resolubilized upon the addition of an aqueous solution for assay of the analyte. Surprisingly, it has been found that treatment of surface-absorbed specific binding proteins with an organic solvent may in some cases increase the capacity of the protein binding partners. In any case, the combination herein of the final step in the known solvent pretreatment method with an element of a conventional specific protein binding assay has rendered the entire assay more convenient and less susceptible to error.

DESCRIPTION OF THE PREFERRED EMBODIMENTS

Any of the organic solvents used previously for solvent extractions may be employed in the improved method of this invention. Other solvents may be employed at the discretion of the user. However, such solvents should not form covalent bonds with the analyte of interest. Further, the analyte should be soluble in the solvent at least to the extent anticipated based upon the analyte concentration range to be encountered in the sample. The halogenated lower alkanes are preferred because their relatively low boiling point expedites evaporation of the solvent from the surface-absorbed protein. It is preferred that the solvents be miscible in water at 20° C. to the extent of less than about 3% v/v, although solvents having a solubility in water of up to about 15% v/v can be used. There is no lower limit to solvent solubility in water.

The use of binding protein physically absorbed to an insoluble surface is an important feature of this invention. Surface-absorbed proteins of this type are well known, as discussed above. U.S. Pat. No. 3,646,346 suggests the use of solid organic polymers such as polystyrene, polyethylene, polypropylene, nitrocellulose and copolymers of acrylonitrile with styrene as suitable absorbent surfaces. This patent is fully incorporated herein by reference. Other polymers will be apparent to the skilled artisan; the polymer need only noncovalently absorb binding proteins, particularly antibodies, without inactivating them. For the purposes of this invention the surface should not be soluble in the organic solvent, even though it may absorb a proportion of the solvent, because the surface is frequently not completely covered with binding protein. For example, if the protein is absorbed only in the bottom of a test tube manufactured from an organic polymer, a solvent should not be used which will attack the exposed polymer.

The tracer to be employed in the specific protein binding assay may be a labelled, water soluble binding protein for the analyte or for a substance which binds the analyte, or it may be a labelled analogue of the analyte. The tracer is ordinarily added to the surface absorbed protein and analyte deposit along with or subsequent to the addition of an aqueous solution to dissolve the analyte deposit. Since the analyte will not bind the surface-absorbed protein in the presence of organic solvent, the reaction between protein and analyte will not commence until an aqueous solution is added. Thus it is best from the standpoint of a competitive-type binding assay to add the tracer in aqueous solution or at approximately the same time as an aqueous solution which might be added for another purpose.

As an example of aqueous solutions which may be added for other purposes, it may be desirable to include in the reaction mixture a serum standard which is free of analyte. This will enable a valid comparison to be made between the unknown and a standard curve prepared from serum standards, i.e., standards which may contain endogenous analyte-binding proteins. Thus the protein effect, if any, will be constant from sample to standards. This artifice will not change the fact that the analyte that is being measured was already extracted from any endogenous analyte-binding proteins present in the original sample.

If the tracer is an analyte analogue, the tracer may be added to the sample before extraction. The tracer will then be co-extracted with any sample analyte. This embodiment is not preferred. It is preferrable to introduce the tracer into the assay after extraction because tracer losses which occur during extraction will be eliminated and the handling of potentially hazardous materials, e.g., radiolabels, is lessened. Thus the solvent ordinarily will be free of tracer when it is contacted with the surface absorbed protein. However, there is at least one circumstance where coextraction of sample and tracer will be useful. If the analyte and its tracer are extracted from the sample at essentially the same rate and degree it is possible to determine the efficiency of extraction by the proportion of label which is extracted into the organic solvent. This procedure for determining the extraction efficiency may be more convenient than the method described in Example 1 and thus may tip the balance in favor of adding the tracer to the unextracted sample, the above disadvantages not withstanding.

The invention will be more fully understood by reference to the following examples.

EXAMPLE 1

Urine samples are prepared for extraction by adding 200 microliters of a well mixed 24-hour urine sample to each of two disposable glass test tubes, one marked "S" and the other "E". The "E" tube is to be used to determine the efficiency of cortisol extraction from the sample. 10 microliters of cortisol standard serum (60 μg%) are mixed with the contents of the "E" tube, and 1.0 ml of chilled methylene chloride is then added to all tubes. The tubes are capped and their contents agitated to aid in the extraction of cortisol into the methylene chloride layer. After separation of the organic phase, duplicate 100 microliter aliquots of the bottom (methylene chloride) layer of each "S" and "E" tube are carefully removed and added to corresponding plastic test tubes coated with rabbit anti-cortisol serum on their lower inner surfaces, also correspondingly labeled "S" and "E". The methylene chloride is then evaporated from the four plastic test tubes by passing a stream of dry air or nitrogen into the tubes or by a mild warming of the extract to about 37° C. The tubes containing dry cortisol residue as prepared above are then assayed as follows.

A set of plastic test tubes coated with rabbit anti-cortisol serum is numbered 1–12. The "S" and "E" tubes from the preparatory steps above are numbered 13–14 and 15–16, respectively. 0.01 ml of the reagents shown in Table 1 below are added to the designated tubes. The cortisol serum blank which is added to each "S" and "E" tube ensures that the protein content of all tubes is equal.

1.0 ml of $^{125}$I-Cortisol 3-(0-carboxymethyl)oxime-L-tyrosine in pH 7.0–7.2 phosphate buffered saline having an activity of about 0.033 $\mu$Ci/ml is added to each tube with gentle mixing. All tubes are incubated in a constant temperature water bath for 45 minutes at 37° C. The contents are removed from the tubes by aspirating or decanting and the tubes counted in a gamma counter with the window suitably adjusted for iodine-125. The results are set forth in Table 1 below.

$$UFC = \frac{"S" (50) (V)}{(10^6) (EE)}$$

of urine added to each antisera-coated tube, V=the total volume of urine collected in 24 hours, and $10^6$ is a conversion factor for pg to $\mu$g. In this example, "S"=785 pg, V=1150 ml/24 hours, EE=0.94. Accordingly, UFC=48 $\mu$g cortisol/24 hours.

EXAMPLE 2

This example demonstrates the effect of various organic solvents on antiserum-coated surfaces. 1 ml of petroleum ether, benzene, ether, ethyl acetate or acetone was added to a selection of cortisol, thyroxine, diphenylhydantoin and estriol rabbit antiserum-coated polypropylene tubes. The solvent level in the tubes was sufficient to immerse the antiserum coated region at the bottom of the tubes. The solvents were equilibrated with atmospheric water vapor. The solvent-containing tubes were then incubated for 3 hours at 50° C. The excess solvent was poured off and the tubes were left overnight to allow the residual solvent to evaporate. Three sets of control tubes were prepared. One set was treated with water in the same manner as the organic solvents, while another set was heated in air for the same period as the liquid-treated tubes. A final set of tubes served as an untreated control. The residual ca-

TABLE 1

| Tube No. | Contents | Cortisol Added (pg/0.01 ml) | CPM Bound | Average Urinary Free Cortisol ($\mu$g/24 hours)* |
|---|---|---|---|---|
| 1 | Cortisol Serum Blank, 0 $\mu$g% | 0 | 27,459 | — |
| 2 | | | 26,396 | |
| 3 | Cortisol Serum Standard, 1.0 $\mu$g% | 100 | 26,030 | — |
| 4 | | | 25,305 | |
| 5 | Cortisol Serum Standard, 3.0 $\mu$g% | 300 | 22,083 | — |
| 6 | | | 21,629 | |
| 7 | Cortisol Serum Standard, 10 $\mu$g% | 1000 | 14,520 | — |
| 8 | | | 14,698 | |
| 9 | Cortisol Serum Standard, 25 $\mu$g% | 2000 | 8,980 | — |
| 10 | | | 9,071 | |
| 11 | Cortisol Serum Standard, 60 $\mu$g% | 6000 | 4,824 | — |
| 12 | | | 5,025 | |
| 13 | Cortisol Serum Blank, 0 $\mu$g% | — | 14,325 | 48 |
| 14 | | | 15,110 | |
| 15 | Cortisol Serum Blank, 0 $\mu$g% | — | 8,009 | — |
| 16 | | | 7,526 | |

*Urinary free cortisol is calculated as follows. First, the results with standards and samples are plotted on semilogarithmic graph paper as counts per minute (CPM) versus cortisol concentrations. The level of cortisol in the "S" and "E" tubes can be determined readily from this plot. The extraction efficiency (EE) is then calculated from the following equation:

$$EE = \frac{"E" - "S"}{600 \text{ pg}}$$

where "E" and "S" are the average pg of cortisol in the extraction efficiency and sample tubes, respectively. In this sample, where "E"=1350 pg and "S"=785 pg, EE=0.94. Finally, the urinary free cortisol (UFC) is calculated in accordance with the equation:

pacity of the antiserum-coated tubes to bind the respective radioiodinated tracers was determined by adding a 1 ml solution of the tracer containing 0.01 $\mu$Ci to each tube containing an antiserum coating specific for that tracer, incubating for 45 minutes at 37° C., carefully decanting the tracer solution and counting the radioactivity bound to the tubes. The percent binding was calculated by dividing the bound counts by the total counts added. The results are shown in Table 2.

TABLE 2

| | % Binding | | | | | | | |
|---|---|---|---|---|---|---|---|---|
| | Solvents | | | | | | | |
| Antiserum | Petroleum Ether | Benzene | Ether | Ethyl Acetate | Acetone | Water | Air | Untreated |
| Cortisol | 55 | 56 | 55 | 54 | 55 | 57 | 56 | 59 |

TABLE 2-continued

| | % Binding | | | | | | | |
|---|---|---|---|---|---|---|---|---|
| | Solvents | | | | | | | |
| Antiserum | Petroleum Ether | Benzene | Ether | Ethyl Acetate | Acetone | Water | Air | Untreated |
| Thyroxine | 50 | 52 | 41 | 41 | 36 | 41 | 39 | 39 |
| Diphenylhydantion | 36 | 34 | 33 | 38 | 43 | 41 | 42 | 43 |
| Estriol | 64 | ND* | 38 | 62 | ND | 57 | 60 | 56 |

ND* = Not Done

Similar results were obtained when the same experiments were repeated with a mixture of 0.2 ml of each organic solvent and 1 ml of phosphate buffered saline in place of the 1 ml of organic solvent.

EXAMPLE 3

This example demonstrates the preparation of a standard curve for testosterone in which the sample extraction solvent is evaporated from contact with antitestosterone-coated polypropylene test tubes. 0.6 ml of serum standards containing 0.1, 0.3, 1, 3 and 10 ng testosterone/ml were mixed with 3 ml of ethyl acetate. The phases were allowed to separate and 0.5 of the ethyl acetate layer was added to each of duplicate antitestosterone-coated tubes. After the ethyl acetate was evaporated under a stream of nitrogen, 1 ml of phosphate buffered saline at pH 7.4 was added to each tube and the testosterone residue dissolved. Five minutes later 0.1 ml of $^{125}$I-labeled testosterone tracer was added to each tube. After incubation for 45 minutes at 37° C., the solution was aspirated from each tube and the bound radioactivity determined in conventional fashion. A virtually straight-line standard curve could be plotted on semi-logarithmic graph paper from the resulting data. The plot was satisfactory for use in the assay of testosterone unknowns.

I claim:

1. In a method for determining the concentration of an analyte in a sample wherein the sample is extracted with a substantially water immiscible organic solvent, the solvent removed from the extract and the extract assayed by a specific protein binding assay, the improvement comprising removing the solvent from the extract while the solvent is in contact with a surface-absorbed binding protein specific for said analyte.

2. The method of claim 1 where the surface is polypropylene.

3. The method of claim 1 wherein the analyte is cortisol or thyroxine and the organic solvent is petroleum ether, benzene, ether, ethyl acetate or methylene chloride.

4. The method of claim 1 wherein the analyte is diphenylhydantoin and the organic solvent is ethyl acetate.

5. The method of claim 1 wherein the analyte is estriol and the organic solvent is petroleum ether or ethyl acetate.

6. The method of claim 1 wherein the organic liquid is removed by evaporation.

7. The method of claim 1 wherein the solvent is selected from the group consisting of carbon tetrachloride, methylene chloride (dichloromethane), ethyl ether, ethyl acetate, petroleum ether, diethyl ether, ether, ethyl acetate, benzene and mixtures thereof.

8. The method of claim 1 wherein the analyte-containing solvent is free of labeled analyte.

9. The method of claim 1 wherein the specific binding protein is an antibody.

10. The method of claim 1 wherein the solubility of the organic solvent in water at 20° C. is less than about 15% v/v.

11. The method of claim 10 wherein the solubility of the organic solvent in water at 20° C. is less than 3% v/v.

12. The method of claim 1 wherein the surface is a solid organic polymer.

13. A method for determining the concentration of cortisol in a sample which comprises;
(a) extracting the sample with a substantially water immiscible organic solvent;
(b) removing at least a portion of said solvent extract to a container having anticortisol absorbed on at least a portion of its inner surface, whereby the anticortisol is contacted with said solvent;
(c) removing the solvent from the container whereby a deposit of extracted cortisol remains in the container; and
(d) conducting a protein binding assay for said cortisol.

14. The method of claim 13 wherein the solvent is methylene chloride (dichloromethane).

15. The method of claim 13 wherein the sample is urine.

* * * * *